United States Patent
Berg et al.

(10) Patent No.: US 6,692,969 B1
(45) Date of Patent: Feb. 17, 2004

(54) METHOD FOR DETECTING, TREATING, AND MONITORING CONDITIONS ASSOCIATED WITH ACTIVATION OF THE COAGULATION RESPONSE

(76) Inventors: David E. Berg, 1101 E. Waltann, Phoenix, AZ (US) 85022; Lois Hill Berg, 1101 E. Waltann, Phoenix, AZ (US) 85022; Harold H. Harrison, 361 Lincoln Ave., Glen Rock, NJ (US) 07452

( * ) Notice: Subject to any disclaimer, the term of this patent is extended or adjusted under 35 U.S.C. 154(b) by 62 days.

(21) Appl. No.: 09/637,808

(22) Filed: Aug. 11, 2000

Related U.S. Application Data

(60) Provisional application No. 60/148,799, filed on Aug. 13, 1999.

(51) Int. Cl.$^7$ ............................................... G01N 33/86
(52) U.S. Cl. ....................................................... 436/69
(58) Field of Search ............................. 514/56; 436/69

(56) References Cited

U.S. PATENT DOCUMENTS

| | | |
|---|---|---|
| 4,451,454 A | 5/1984 | Wong |
| 5,834,215 A | 11/1998 | Garry et al. |
| 5,846,758 A | 12/1998 | Medenica |
| 6,107,280 A | 8/2000 | White et al. |

OTHER PUBLICATIONS

Mannucci, British Medical Bulletin 50(4): 851–870 (1994).*
Cohen et al., Am. J. Cardiol. 66(19): 1287–1292 (1990). Abstract.*
Berkow, et al. The Merck Manual of Diagnosis and Therapy, published 1992, pp. 678–679.
Berkow et al., The Merck Manual of Diagnosis and Therapy, published 1992, pp. 154–157; 841–845; 1312–1313; 1402–1407; 1488–1490; 1495–1500;2102–2105; and 2267–2268.
Vecchi et al. Risk of Thromboembolic Complications in Patients with Inflammatory Bowel Disease, University of Milan, Milan, Italy, Int J Clin Lab 1991 vol. 21, No. 2, Res 21:165–170.
Lip et al., Increased Markers of the Thrombogenesis in Chronic Atrial Fibrillation: Effects of Warfarin Treatment,. British Heart Journal 1995; vol. 73, No. 6, pp.: 527–533.
Fon et al., Hemostatic Markers in Acute Transient Ischemic Attacks, Stroke. Feb. 1994, vol. 25, No. 2, pp. 282–286.
Berg et al., Monitoring of Heparin Therapy by Soluble Fibrin Monomer (SFM) Levels in Infertila Women Who Became Pregnant and Carried Their Pregnancies to Full Term Delivery on Heparin: A comparison of Quantitative Versus Semiquantitative Methods for SFM., Blood, vol. 90, No. 10, Suppl. 1, part 2, p. 111b abstract 3207.
Takahashi et al., Evaluation of Oral Anticoagulant Therapy by Measuring Plasma prothrombin Fragment 1+2, Blood Coagulation and Fibrinolysis, vol. 4, No. 3,, 1993, pp. 435–439.
Sakata et al., Suppression of Plasma–Activated Factor VII Levels by Warfarin Therapy,. Arteriosclerosis, Thrombosis and Vascular Biology, vol. 15, No. 2, Feb. 1995, pp. 241–246.
Kahn et al., Nonvalvular Atrial Fibrillation: Evidence for a Prothrombotic State, Canadian Med Assoc.. J. Sept., 1997 vol. 157, No. 6, pp. 673–681.
Berg et al., Chronic Fatigue Syndrome and/or Fibromyalgia as a Variation of Antiphospholipid Antibody Syndrome: An Explanatory Model and Approach to Laboratory diagnosis. Blood Coagulation and Fibrinolysis 1999, vol. 10, No. 7, pp. 435–438.
Bona et al., Thrombin Generation and Activity are Increased in Patients with Cancer Receiving Sodium Warfarin as Secondary Propylaxis Against Venous Thrombosis. Blood, 1997, vol. 90, No. 10, Suppl. 1, Part 2 p. 111b, abstract 3207.
Berg et al., Identification of chronic fatigue syndrome (CFS) and Fibromyalgia (FM) as a Low Grade Hypercoagulable State: A Multi–Center, Blinded Random Study. Thrombosis and Haemostasis, Journal of the International Society on Thrombosis and Haemostasis, Abstracts, Supp. Aug. 1999, p. 317.

* cited by examiner

Primary Examiner—Jean C. Witz
(74) Attorney, Agent, or Firm—Parsons & Goltry; Michael W. Goltry; Robert A. Parsons

(57) ABSTRACT

This invention relates to a method for using a novel combination of assays to detect minimal activation of the coagulation response for determining whether a patient whose initial clinical evaluation indicates chronic fatigue syndrome, fibromyalgia, and related conditions can be treated using anticoagulant therapies. If activation of the coagulation response is detected, the present invention further includes treatment of CFS, FM or related condition using anticoagulant therapies.

8 Claims, No Drawings

METHOD FOR DETECTING, TREATING, AND MONITORING CONDITIONS ASSOCIATED WITH ACTIVATION OF THE COAGULATION RESPONSE

This Non-Provisional Application claims the benefit of U.S. Provisional Application Serial No. 60/148,799 filed on Aug. 13, 1999. This invention relates to methods for detecting, treating, and monitoring conditions associated with activation of the coagulation response which respond to anti-coagulant therapy.

FIELD OF THE INVENTION

BACKGROUND OF THE INVENTION

Chronic fatigue syndrome (CFS) and fibromyalgia (FM) have been considered diagnoses of exclusion where no other diagnosis fit well. CFS has been defined by specific requirements of fatigue, its duration, associated symptoms, and initial clinical and laboratory evaluation. There has existed no reliable laboratory means for determining whether an individual was suffering from CFS, FM, or some other disease. Accordingly, a felt need for a method of testing for CFS and FM existed.

SUMMARY OF THE INVENTION

This invention relates to a method for using a novel combination of assays to detect minimal activation of the coagulation response for determining whether a patient whose initial clinical evaluation indicates chronic fatigue syndrome, fibromyalgia, and related conditions can be treated using anticoagulant therapies. If activation of the coagulation response is detected, the present invention further includes treatment of CFS, FM or related condition using anticoagulant therapies.

We have discovered that we may reliably diagnose a patient suffering from CFS or FM by evaluating the status of the coagulation response in that patient by using a novel combination of tests which can detect minimal activation of the coagulation response in a patient. This novel combination includes tests for determining levels of fibrinogen, prothrombin fragment 1+2, thrombin/antithrombin complexes, soluble fibrin monomer, and platelet activation by flow cytometry. These assays are highly sensitive to minimal deviation from normal. Deviation from the normal values in any two of the five assays permits diagnosis of CFS, FM, or other disease associated with activation of the coagulation response.

Once a condition associated with activation of the coagulation response has been diagnosed, the patient is treated with anticoagulant therapy, such as heparin followed by warfarin or warfarin alone. Coumarins or coumarin derivatives may also be used. Heparin can be defined as heparin (porcine or bovine) or any of its derivatives, such as low molecular weight heparin (LMWH), oral heparin, heparinoids, or any other designer heparin-like drugs. It is presently preferred that a low dose anticoagulant therapy be used. Patient progression and recovery is then monitored using the novel combination of assays.

We postulate that a majority of individuals diagnosed as CFS and/or FM on clinical criteria may be defined as having antiphospholipid antibody syndrome (APS) with endothelial cells as a major disease target with or without platelet activation. Laboratory findings in patients suffering with APS include anticardiolipin antibodies, lupus anticoagulants, antiphosphatidylserine antibodies, anti-B2GPI antibodies. Clinical findings include thrombocytopenia, neurological complications, venous thrombosis, arterial thrombosis, and/or recurrent fetal loss. Patients with primary APS (PAPS) presently have no clinical or laboratory evidence of another definable autoimmune disease. Antiphospholipid antibodies have long been associated with a hypercoagulable state, involving both procoagulant activity as well as inhibition of anticoagulant and fibrinolytic activity. In CFS and/or FM patients, the principal antibodies found to date are the anti-B2GPI antibodies. This precedes the generation of a hypercoagulable state based on our proposed model.

Endothelial cells are protected in the microvascular circulation by $B_2GPI$ and Annexin V proteins. This protective layer helps endothelial cells maintain an anticoagulant environment. Exposure to pathogens, such as herpes viruses (HV, HHV6, EBV), cytomegalovirus (CMV), mycoplasma, chlamydia pneumonia, or some vaccines can result in both active persistent infection and latent infection in mononuclear and endothelial cells. Some pathogens like CMV and HV constitutively express phosphatidylserine-like procoagulant activity, capable of binding Xa and Va to form the prothrombinase complex. HHV6 is found in about 70% of all CFS patients. In several studies, this same 70% infection rate is seen in multiple sclerosis patients with HHV6. HHV6 is also implicated in chronic myelopathy. Endothelial cells serve as a reservoir for harboring HHV6. Infected endothelial cells lose the ability to synthesize prostacyclin with associated incapacity to deter platelet adhesion. In addition, CMV and HV express tissue factor antigen on each virus surface. HV can induce a prothrombotic phenotype in vascular endothelial cells. This phenotype markedly reduces heparin sulfate protcoglycan synthesis and surface expression by endothelial cells. Thrombomodulin expression is also reduced in infected endothelium. Due to fibrin deposition, fibrinolysis activation may also be diminished. Activation of endothelial cells is seen by surface expression of P-selectin and von Willebrand Factor (vWF). Thrombin generated after the assembly of the prothrombinase complex on the virus-infected endothelium mobilizes vWF from the Weibel-Palade body to the endothelial cell surface, where it acts as a platelet receptor. Cell-independent thrombin generation may be the earliest event in vascular pathology mediated by HV.

Because exposure and expression of phosphatidylserine (PS) is part of the infectious process, those exposed phospholipids activate the immune system to form antiphospholipid antibodies. The primary targets of these immunoglobulin (Ig)G, IgM and IgA antibodies are the protective proteins for endothelial cells, specifically B2GPI and Annexin V. As with other APS diseases, there is an increased incidence of thrombocytopenia in HHV6 patients. With the loss of this protective layer due to APL antibodies, coagulation proteins can bind, react and form thrombin (IIa). If this process is not property inhibited (thrombin-antithrombin complexes), then excess thrombin can convert fibrinogen to soluble fibrin monomer (SFM). SFM is a sticky protein that increases blood viscosity and can coat endothelial cells surfaces as fibrin or fibrinoid material. Patients with CFS and FM symptoms typically have a hypercoagulable state demonstrated by increased markers of coagulation activation and increased blood viscosity due to the generation of soluble fibrin monomer (SFM). Once CFS and FM is diagnosed using our combination of assays, CFS/FM patients may be treated with anticoagulant therapies, and their treatment and recovery monitored using our combination of tests.

Patients with immune mediated chronic inflammatory disorders of many types can have low level activation of the coagulation response. Therefore, patients with a spectrum of chronic inflammatory processes may have low level activation of coagulation as part of their pathophysiology. We postulate that our tests for activation of the coagulation and platelet systems also have application to other conditions which stem from activation of the coagulation response. This has been validated by preliminary studies of patients suffering with multiple sclerosis, breast implant sickness syndrome, fetal wastage syndrome, gulf war illness, inflammatory bowel disease, autism. As with CFS and FM, once diagnosed using our combination of assays, these patients may be treated with anticoagulant therapies, and their treatment and recovery monitored using our combination of tests.

We postulate that our combination of tests for detecting minimal activation of coagulation response also has application to detecting and treating, Sjogrens syndrome, late Lyme disease (also called chronic Lyme disease), transient ischemic attack, attention deficit disorder, Alzheimer's disease, Parkinson's disease, as well as some cardiovascular diseases. Once diagnosed using our combination of assays, these patients should also benefit from treatment with anticoagulant therapies, and their treatment and recovery monitored using our combination of tests.

The Presently Preferred Assays Used To Determine Minimal Activation of Coagulation Response Although thrombin generation is among the first steps in the coagulation response, thrombin itself is difficult to quantify because it lasts only 30 seconds in the blood circulation. Consequently, other measurable components of the coagulation response must be considered. (1) Prothrombin fragment 1+2, which is released when prothrombin is converted into thrombin, can be used to indicate activation of the coagulation response. (2) Increased levels of thrombin/antithrombin complexes (TATs) also indicate thrombin generation and an attempt to remove excess thrombin. Thus, an increased level of TATs also indicates activation of the coagulation response. (3) When excess thrombin is generated by the coagulation response, fibrinogen is cleaved to soluble fibrin monomer (SFM). Accordingly, increased levels of SFM also indicate activation of the coagulation response. (4) With the consumption of fibrinogen, the body may compensate by increasing fibrinogen levels slightly above the normal range; therefore, increased fibrinogen levels are also an indicator of activation of the coagulation response. (5) Finally, platelet activation may also be used as an indicator of coagulation response activation.

The tests discussed above are the assays presently preferred, it being understood that other tests sensitive to minimal activation of the coagulation response may be substituted for the assays discussed.

DETAILED DESCRIPTION OF THE INVENTION

For the purposes of describing the invention, we discuss the form of the method of the present invention which is presently preferred; it being understood, however, that this invention is not limited to the precise arrangements, instrumentalities, and assays discussed.

Our new method for diagnosing CFS, FM, and related conditions uses a novel combination of assays for detecting minimal activation of the coagulation response. Highly sensitive tests are used which are capable of detecting minimal deviations from normal levels of fibrinogen, prothrombin fragment 1+2, thrombin/antithrombin complexes, soluble fibrin monomer, and platelet activation by flow cytometry, platelet aggregation, or related techniques. According to our invention, if a patient receives an initial clinical evaluation indicating CFS and/or FM and if 2 or more of the above assays show abnormal results, that patient can be reliably diagnosed with CFS and/or FM. Once a condition has been diagnosed that is responsive to anticoagulant therapy, the patient is treated with low dose anticoagulant therapy, such as heparin followed by warfarin, or pharmacologically and conceptually similar anticoagulant regimens. Patient progression and recovery is then monitored using the novel combination of assays.

In order to test our method, we have conducted a blinded study of 54 CFS and/or FM patients and 23 controls, for a total of 77 individuals. According to our method, blood drawn from all individuals was subjected to each of the 5 tests. Using our presently preferred combination of 5 assays, we determined that the CFS and FM patients could be reliably distinguished from the controls. Individuals whose blood tested outside of the normal range for 2 or more of the 5 tests were diagnosed as suffering from CFS and/or FM. 22 of the 23 controls were correctly identified. One control was positive in two assays for a false positivity rate of 4%. Of the 54 patients with CFS or FM, 4 had normal values, for a false negative rate of 7.4%. This shows that 92+% of CFS and/or FM patients had a demonstrable hypercoagulable state.

The following table sets out the mean values for each group tested.

| TESTS: | | FIB mg/dl | F1 + 2 nM | T/AT ug/l | SFM nmol/l | PA (Platelet Activation) | CD62P % |
|---|---|---|---|---|---|---|---|
| Reference Range | Normal | <310 | <1.1 | 1.0–4.1 | <20 | Normal | <26 |
| Controls #Abnormal/Normal | 23 | 280 2/23 | 1.0 3/23 | 1.6 4/23 | 10 3/23 | 0% Positive 0/23 | 17.5 5/23 |
| Patients #Abnormal/Normal | 54 | 367 45/54 | 1.2 26/54 | 1.6 25/54 | 22 32/54 | 42% Positive 22/54 | 22 21/52 |
| P Value | | <0.001 | <0.005 | <0.025 | <0.001 | <0.001 | <0.10 |

As stated above, in CFS and FM patients, the principal antibodies found to date are the anti-B2GPI antibodies. Anti-B2GPI antibodies can precede the generation of a hypercoagulable state. In a normal capillary endothelial cell, phosphatidylserine is on the inside of the cell membrane.

When phosphatidylserine is transported to the surface of the endothelial cell, it is isolated from blood flowing through the vessels by a layer of B2GPI and Annexin V proteins, which cover the phosphatidylserine. When the immune system is activated, anti-B2GPI and anti-annexin V antibodies, collectively antiphospholipid antibodies, are generated. These antibodies are IgG, IgA, and IgM, the majority of which bind to the B2GPI and annexin V proteins dislodging them from the phosphatidylserine. When the phosphatidylserine on the vessel walls is exposed, coagulation factor tenase and prothrombinase complexes bind to the surfaces of the endothelial cells which coat the vessel walls. When prothrombin complexes bind to the cell walls, prothrombin is converted to thrombin, which releases the activation peptide prothrombin fragment 1+2.

The human body responds to the generation of excess or inappropriate thrombin levels by synthesizing the inhibitor antithrombin. Antithrombin combines with thrombin to form thrombin/antithrombin complexes, which are then removed from the blood. Antithrombin is a slow inhibitor of thrombin, but in the presence of heparin, antithrombin reacts with thrombin at a greatly increased rate. Activated protein C/antitrypsin complex is a secondary inhibitor of thrombin generation.

When more thrombin is generated than can be removed by the thrombin inhibitors, thrombin reacts with fibrinogen to create an intermediate protein called soluble fibrin monomer. Soluble fibrin monomer is a sticky protein which increases blood viscosity and forms deposits on capillary wall endothelial cells. The soluble fibrin monomer which is deposited on the capillary walls, a phenomenon called fibrin deposition, may block the passage of nutrients through the capillary walls to the surrounding tissues, whether it is another capillary, muscle or organ tissue. We postulate that the increase in blood viscosity in combination with associated blockage in nutrient transfer results in the fatigue of CFS and the muscle pain of FM. This could also be part of the explanation (pathology) of fetal demise and spontaneous abortions seen in recurrent miscarriages (fetal wastage syndrome).

In addition to the creation of soluble fibrin monomer, thrombin also activates factor XIII to XIIIa in the blood, causing it to react with the soluble fibrin monomer to create insoluble fibrin strands, which may in turn generate a clot or fibrin deposition on vascular walls, further inhibiting blood flow and nutrient transfer. Once fibrin deposition or blood clot formation occurs, it becomes necessary to dissolve the fibrin. Protein C, which is activated by the excess thrombin production, helps to activate the fibrinolytic system when tissue plasminogen activator converts the protein plasminogen into plasmin. Plasmin is a very potent enzyme for fibrin depositions or clots and keeps the circulatory system of blood vessels open and clean. Tissue plasminogen activator is conventionally injected into patients to dissolve blood clots, such as heart attacks, myocardial infarctions, strokes, blood clots in the eye, etc.

Platelet activation within the blood is also a contributing factor in thrombin formation. Platelet activation reinforces the generation of thrombin by providing a major surface for thrombin formation. Platelets may be directly activated by the immune system when immunoglobulins activate glycoprotein receptors and cause platelets to become "sticky". This "sticky state" can result in fibrin formation, vascular and endothelial cell changes, and, at times, platelet clumping. Platelet activation can be measured by a special laboratory procedure called flow cytometry, platelet aggregation or related techniques.

Differences in genetic makeup are the most likely reason that all people exposed to an immune system activating pathogen do not develop diseases associated with a hypercoagulable state, such as chronic fatigue syndrome and fibromyalgia. Patients who have a hereditary deficiency for thrombophilia or hypofibrinolysis may be unable to properly control thrombin generation. Genetic defects in the proteins which regulate the coagulation process, are most likely the cause of long term activation of the immune system which results in a persistent hypercoagulable state. Thrombophilia may be caused by one or more genetic abnormalities in proteins which presently include protein C, protein S, antithrombin, factor V leiden, factor II gene mutation, thrombomodulin, heparin cofactor II, or factors II, VII, IX, X, XI, XII, and others which may be found for related genes. Hypofibrinolysis may be caused by one or more genetic abnormalities factors which presently include plasminogen, tPA, urokinase, PAI-1, lipoprotein(a), homocysteine, factor V leiden, factor XI, and TAFI, and others which may be found for related genes.

Patients with immune mediated chronic inflammatory disorders of many types can have low level activation of the coagulation response. Therefore, patients with a spectrum of chronic inflammatory processes may have low level activation of coagulation as part of their pathophysiology. We postulate that our tests for activation of the coagulation and platelet systems also have application to other conditions which stem from activation of the coagulation response. This has been validated by preliminary studies of patients suffering with multiple sclerosis, breast implant sickness syndrome, gulf war illness, inflammatory bowel disease, autism, and fetal wastage syndrome. As with CFS and FM, once diagnosed using our combination of assays, these patients may be treated with anticoagulant therapies, and their treatment and recovery monitored using our combination of tests. We propose that a common feature of these conditions is the chronic inflammatory process that stimulates low level activation of coagulation.

The following table sets out our preliminary findings for autism, attention deficit disorder, multiple sclerosis, Parkinson's disease, Sjogrens syndrome, and gulf war illness. Individuals who were diagnosed as suffering from one of these chronic inflammatory disorders tested outside of the normal range for 2 or more of the 5 tests in our method.

| Disease | TESTS | Number of Individuals Tested | FIB mg/dl | F1 + 2 nM | T/AT ug/l | SFM nmol/l | PA (Platelet Activation) |
|---|---|---|---|---|---|---|---|
| Autism | #Abnormal/Normal | 3 | 1/3 | 3/3 | 0/3 | 3/3 | 0/3 |
| Attention Deficit Disorder | #Abnormal/Normal | 2 | 1/2 | 1/2 | 1/2 | 1/2 | 0/2 |
| Multiple Sclerosis | #Abnormal/Normal | 3 | 1/3 | 1/3 | 2/3 | 2/3 | 0/3 |
| Parkinson's Disease | #Abnormal/Normal | 2 | 1/2 | 1/2 | 1/2 | 0/2 | 0/2 |
| Sjogrens Disease | #Abnormal/Normal | 1 | 1/1 | 0/1 | 0/1 | 1/1 | 0/1 |
| Gulf War Illness | #Abnormal/Normal | 33 | 17/33 | 11/33 | 6/33 | 17/33 | 15/33 |

We postulate that our combination of tests for detecting minimal activation of coagulation response also has application to detecting and treating other immune mediated chronic inflammatory disorders such as Siogrens syndrome, late Lyme disease (also called chronic Lyme disease), transient ischemic attack, attention deficit disorder, Alzheimer's disease, Parkinson's disease, as well as some cardiovascular diseases. Once diagnosed using our combination of assays, these patients should also benefit from treatment with anticoagulant therapies, and their treatment and recovery monitored using our combination of tests.

We claim:

1. A method for assisting in the diagnosis of chronic fatigue syndrome or fibromyalgia by determining a low level activation of the coagulation response comprising the steps of:
   a. performing a panel of four quantitative blood tests comprising (1) fibrinogen, (2) prothrombin fragment 1+2, (3) thrombin/antithrombin complexes, and (4) soluble fibrin monomer;
   b. observing the test results from the panel to determine whether two or more test results are abnormal, thereby indicating a low level activation of the coagulation response.

2. The method of claim 1 further comprising the steps of comparing clinical data with the test results to confirm the diagnosis of a sub-thrombotic condition.

3. The method of claim 2 further comprising monitoring the recovery of the patient by repeating the tests for which the initial results were abnormal.

4. The method of claim 1 wherein said method is performed to screen a population in need of a clinical work-up.

5. A method for assisting in the diagnosis of chronic fatigue syndrome or fibromyalgia by determining a low level activation of the coagulation response comprising the steps of:
   a. performing a panel of four quantitative blood tests comprising (1) fibrinogen, (2) prothrombin fragment 1+2, (3) thrombin/antithrombin complexes, (4) soluble fibrin monomer, and (5) platelet activity by flow cytometry;
   b. observing the test results from the panel to determine whether two or more test results are abnormal, thereby indicating a low level activation of the coagulation response.

6. The method of claim 5 further comprising the steps of comparing clinical data with the test results to confirm the diagnosis of a sub-thrombotic condition.

7. The method of claim 5 further comprising monitoring the recovery of the patient by repeating the tests for which the initial results were abnormal.

8. The method of claim 5 wherein said method is performed to screen a population in need of a clinical work-up.

* * * * *